United States Patent
Doubler et al.

(10) Patent No.: US 6,355,068 B1
(45) Date of Patent: Mar. 12, 2002

(54) SIGHT GAUGE MODULAR JOINT AND METHOD

(75) Inventors: Robert L. Doubler, Ida, MI (US); John E. Hammill, Sr., Rossford, OH (US)

(73) Assignee: Hammill Manufacturing Co., Toledo, OH (US)

( * ) Notice: Subject to any disclaimer, the term of this patent is extended or adjusted under 35 U.S.C. 154(b) by 0 days.

(21) Appl. No.: 09/876,437

(22) Filed: Jun. 7, 2001

(51) Int. Cl.[7] .................................................. A61F 2/32
(52) U.S. Cl. ................................ 623/22.42; 623/23.18
(58) Field of Search ........................... 623/22.4, 22.41, 623/22.42, 22.43, 22.44, 22.45, 22.46, 23.15, 23.18

(56) References Cited

U.S. PATENT DOCUMENTS

| | | | |
|---|---|---|---|
| 4,851,007 A | * | 7/1989 | Gray ...................... 623/22.46 |
| 5,181,928 A | * | 1/1993 | Bolesky et al. ........... 623/22.42 |
| 5,653,765 A | | 8/1997 | McTighe et al. |
| 5,725,592 A | | 3/1998 | White et al. |
| 5,876,459 A | | 3/1999 | Powell |
| 5,906,644 A | * | 5/1999 | Powell ...................... 623/22.42 |
| 5,931,871 A | * | 8/1999 | Baur et al. ................. 623/22.4 |
| 6,102,956 A | * | 8/2000 | Kranz ...................... 623/23.15 |

\* cited by examiner

*Primary Examiner*—David J. Isabella
(74) *Attorney, Agent, or Firm*—McHale & Slavin

(57) ABSTRACT

A modular prosthesis has an intramedullary rod element which is to be inserted in a bone. The rod has a shaped proximal portion which is telescoped into one end of a bore in the body element. The mating surfaces of the shaped rod and the body bore form a rotationally immovable connection. A neck element is telescoped into the other end of the body bore. The neck and the body have mating planar surfaces visually discernable as being spaced apart. The neck and body have complementary tapered walls. The prosthesis is subjected to compression to eliminate the visual gap and produce a rigid area seal. All the elements are secured together by a compression screw through the neck, body and rod.

7 Claims, 3 Drawing Sheets

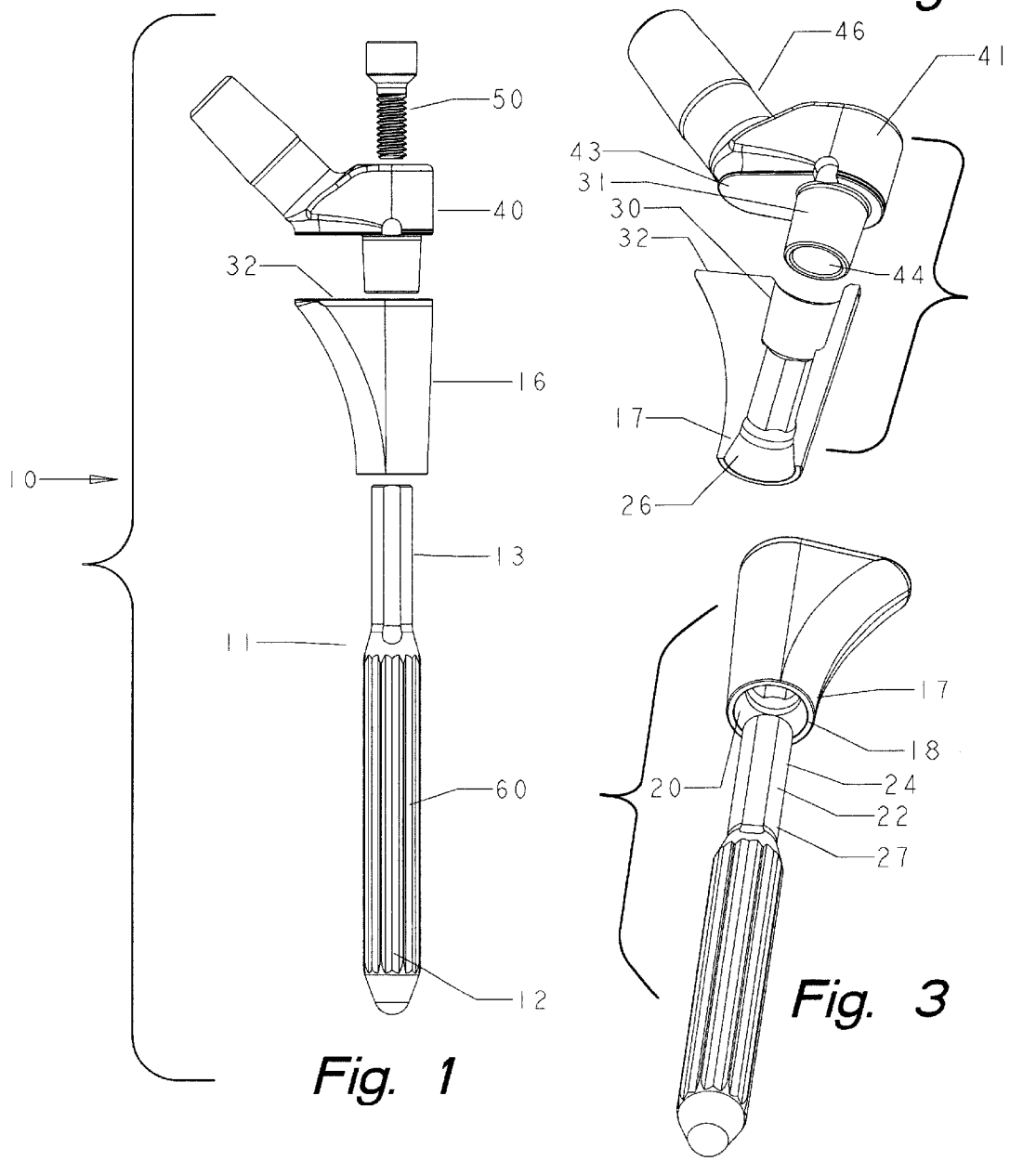

*Fig. 5*
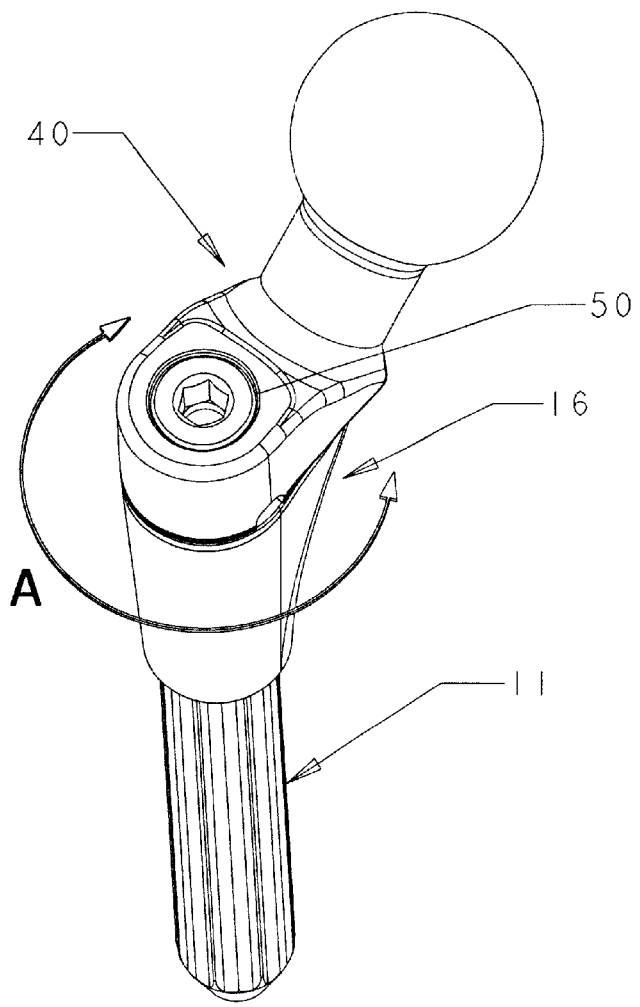
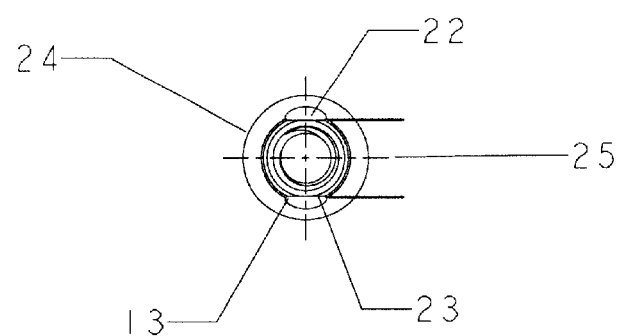
*Fig. 4*

SIGHT GAUGE MODULAR JOINT AND METHOD

This application is related to U.S. application Ser. No. 09/527,180, filed Mar. 17, 2000, the contents of which are incorporated by reference.

FIELD OF THE INVENTION

This invention relates to the medical field of orthopaedics and joint replacement, in particular. Modular artificial joints have several components that must be assembled and placed in the patient to reconstruct a joint. While modular joints provide the ability to custom fit an artificial joint to a patient's anatomy, the connection between the components must be without relative movement after implantation. This invention is directed to a modular artificial joint construction and method which provide a locking mechanism to secure the components immovably together and a visual indication that the components are properly assembled.

BACKGROUND OF THE INVENTION

In replacing a hip joint, the head of the femur is removed along with the ball. The trochanter portion of the femur is shaped and prepared for receiving the prosthesis so that the artificial joint will closely approximate the natural hip.

Earlier artificial hip joints were made of one-piece construction requiring a large inventory of prosthesis to accommodate the various sized patients. The modular artificial joint has two or three or more elements which replace the natural hip. By manufacturing these components with interchangeable connections but different external sizes, inventories may be smaller because of the ability to mix and match components. Also, the modular prosthesis provides more flexibility in customizing the various components of a joint to the various parts of a patient's natural joint.

In a three piece artificial hip joint, the various sized components of the joint that may be selected are the intramedullary rod, the trochanter and the neck. The intramedullary rod is inserted into the end of the femur. The rod acts as a stabilizer in maintaining the artificial joint in the axis of the femur. The upper portion of the rod which extends toward the proximal end of the femur is fitted into a trochanter element which is shaped like the removed broad head of the femur which it replaces. This element, along with the rod, is used to adjust the length of the prosthesis to approximate the natural length of the femur.

The natural trochanter is the broadened area offset from the end of the femur. The natural trochanter may be at any radial angle about the axis of the femur. This natural angular relationship must be reproduced by the intramedullary rod and the artificial trochanter. The artificial trochanter is seated on the end of the patient's femur and is the main load bearing element of the prosthesis. It is important that this load, which is mostly compression, is transmitted along the axis of the femur.

A neck element is inserted into the trochanter element and carries an extension onto which the ball joint will be fixed. The horizontal angle between the trochanter and the neck extension is variable to reproduce the anteversion angle of the patient's natural joint. The neck carries cantilevered forces in torque and compression between the acetabulum and the trochanter. It is also important that these forces do not result in relative movement between the trochanter and the neck.

All these elements have a central bore and are permanently secured together by a compression screw which is inserted into the neck element, extends through the trochanter element, and is threaded into the upper end of the rod. In some cases, the intramedullary rod may be attached to the bone with bone cement while, in other cases the cement is omitted.

When the cement is omitted, the placement and fixation of the intramedullary rod becomes more critical to pain free usage of the prosthesis. Further, it is most important that the intramedullary rod not be disturbed after insertion since this would corrupt the union between the rod and the interior of the femur.

In order to maintain the original union between the femur and the intramedullary rod, modular prosthesis have been developed to allow rotational adjustment of the several parts or elements about the rod before the placement of the prosthesis to more closely reproduce the natural structure of the hip. The modular concept also allows the selection of different sized elements, before or during surgery, to more closely approximate the natural joint.

With the advantage of flexibility gained by modular prosthesis, there comes the requirement that there be no movement between the several parts or elements after implantation. These movements may cause misalignment of the joint resulting in increased pain, trauma to the joint and, even, dislocation of the joint.

In a modular hip prosthesis, the neck is subjected to cantilevered forces of torque and compression which are transmitted to the body of the prosthesis at the junction between the neck and body. If there is any angular movement between the neck and body at this junction, these forces are magnified and transmitted to the junction between the body and the bone thereby degrading the entire prosthesis. Prosthesis which have line seals or screw thread unions between these elements of the prosthesis are subject to relative movement between the elements. For example, when two cones are telescoped together the junction is a circular line seal about the circumference of the cones. This union can pivot about the line seal. Similarly, when a bolt or screw is used to tighten a connection between two pieces, the leading threads take most of the stress which is not evenly distributed along the shaft of the bolt.

DESCRIPTION OF THE PRIOR ART

The prior art is replete with artificial prosthesis and hip joints, in particular.

Illustrative of the state of the art are U.S. Pat. No. 5,725,592 to White et al, U.S. Pat. No. 5,876,459 and U.S. Pat. No. 5,506,644 to Powell which disclose modular hip joints having a stem, one end of which is inserted in the intramedullary canal. The other end of the stem is tapered to fit within a second, neck, element. The neck ultimately supports the ball joint. A sleeve element is placed over the junction of the first two-elements. All three elements are rotationally movable relative to each other. A bolt is driven through the bore of the neck and stem to fix the elements together.

In the Powell patents the bolt deforms a portion of the interconnected elements for a friction fit between the neck and the stem. These prior art patents disclose that the sleeve may have a polygonal shaped bore with the articulating elements having corresponding shaped portions. The interconnected elements of these hip joints do not form a static lock between each other but require a deformation of one or more elements before a friction fit is established. The deformation and friction fit is between the stem and the neck rather than the sleeve and the stem.

U.S. Pat. No. 5,653,765, to McTighe et al discloses a modular hip joint with a stem, an intermediate shoulder portion, and a proximal shoulder piece which attaches to the ball. The stem and the intermediate shoulder portion have interengaging teeth on the corresponding ends of each by which they are connected. This end-to-end connection allows for rotational movement of the elements relative to each other. The proximal shoulder piece and the intermediate shoulder piece also have an end-to-end toothed connection for rotational adjustment. This construction has two movable end-to-end connections which provide good flexibility for rotation of the elements but have small surface areas of fixation to each other limited to the surfaces of the interengaged teeth.

U.S. Pat. No. 4,851,007 to Gray discloses a modular hip prosthesis with a tapered fit between the intramedullary rod and the neck. In this prosthesis, there is no bolt used to fix the elements together.

SUMMARY OF THE INVENTION

In the instant invention a modular prosthesis is taught which has an intramedullary rod element which is to be inserted in a bone. The rod has a shaped proximal portion which is telescoped into one end of a bore in a body or trochanter element. The mating surfaces of the shaped rod and the body bore form a rotationally immovable connection. A neck element is telescoped into the other end of the body bore permitting rotational adjustment. All the elements are locked together by a compression screw through the neck and rod.

The method steps involve choosing the proper sized elements for a best-fit intra-operative prosthesis for the patient. The elements are combined together in an initial friction fit assembly in which the elements are relatively movable. This assembly leaves a slight gap between the neck and the body or trochanter. This gap can be visualized as a gauge of the final assembly of the prosthesis. When all the variables of the patient's anatomy are replicated in the assembly, the prosthesis is subjected to a much greater longitudinal compression which closes the gap and fixes the elements immovably together. The compression screw is then inserted and torqued down to hold the elements in the assembled condition. The surgeon can visually check the prosthesis before implantation to verify that the assembly is complete and the elements are immovable with regard to each other.

The invention can be used as a prosthesis for various long bones in the body including, but not limited to, the femur, humerus, tibia, and fibula. The invention will be explained in relation to the femur.

In a particularly preferred embodiment of the instant invention a modular prosthesis is described for use as a hip replacement having an intramedullary rod, a trochanter and a neck. The intramedullary rod has a distal end adapted for insertion into the intramedullary canal of the femur and a proximal end. The proximal end has a reduced radius and a circumference with opposite planar surfaces joined by curved surfaces. The proximal end includes a screw threaded blind bore along the longitudinal axis of the intramedullary rod.

The trochanter or body has a narrow distal end and a larger proximal end forming an external shape approximating the natural bone. The artificial trochanter has a through bore from the distal end to the proximal end, with the proximal and distal ends of the through bore being tapered and having a smooth circumference. The intermediate portion of the through bore has a circumference with opposite planar sides joined by curved surfaces. The circumference of the trochanter bore and the circumference of the proximal end of the intramedullary rod telescope together with the opposite planar surfaces in intimate contact with each other forming a rotationally secure connection with the artificial trochanter approximating the position of the natural trochanter.

The neck has a conical extension about a through bore adapted to be inserted into the proximal end of the through bore of said trochanter. The proximal end of the through bore of the body or trochanter is tapered. The tapers of the conical extension and the through bore are complementary in size and shape. The through bore extension of the neck and the proximal end of the through bore in the trochanter telescope together forming an initially rotationally adjustable connection.

The proximal end of the through bore in the neck has an enlarged countersunk bore and the distal end of the through bore telescopes over the proximal end of the intramedullary rod. The initial assembly has a visually discernable gap between the distal end of the neck and the proximal end of the body or trochanter.

Upon completion of all adjustments necessary for the prosthesis to approximate the natural bone, final assembly is carried out with substantial longitudinal compression of the entire prosthesis sufficient to close the visual gap and force fit the complementary tapered walls of the neck and the body together in an area seal.

A threaded compression screw is disposed in the countersunk bore and threadably engaged with the screw threads in said proximal end of said intramedullary rod forming a locked integral prosthesis. The compression screw is turned until a recommended ft-lbs of torque is achieved.

Accordingly, it is an objective of the instant invention to provide an artificial joint with an intramedullary rod element which is connected with the body or trochanter element in such a manner as to prevent any relative movement between the elements. Rotational movement, in this context, refers to the turning of either element in a plane normal to the common longitudinal axis of the elements.

It is a further objective of the instant invention to provide the body or trochanter and the neck with a locking mechanism to rigidly secure the components together to prevent relative rotation.

It is another objective of this invention to provide a compression screw engaging the neck and the intramedullary rod through the intermediate body thereby securing the assembly with a particular torque value.

It is a still further objective of the invention provide a method of assembly of the elements to provide for adjustments peculiar to an individual and final assembly into a rigid prosthesis.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 1 is an exploded perspective of the prosthesis of this invention;

FIG. 2 shows an exploded perspective of the trochanter and neck of the prosthesis;

FIG. 3 is an exploded perspective view of the neck and intramedullary rod of the prosthesis of this invention;

FIG. 4 shows a cross section of the proximal end of the intramedullary rod of this invention;

FIG. 5 shows a top perspective showing anteversion angle;

DETAILED DESCRIPTION OF THE INVENTION

Figure 6:
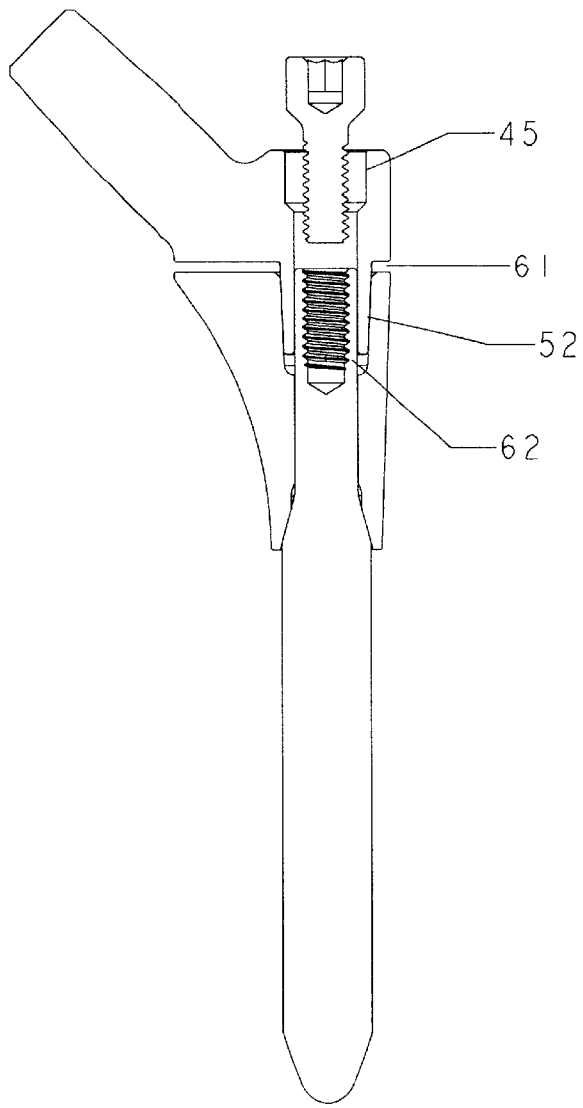
FIG. 6 shows a cross section of the assembled prosthesis with a gap.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

The prosthesis 10, shown in FIG. 1, has an intramedullary rod 11 which provides stability. The rod has a distal end 12 and a proximal end 13. The proximal end of the rod is smaller in diameter than the distal end. The distal end 12 is inserted into the patient's femur and forms the stabilizing connection for maintaining the prosthesis in alignment with the axis of the femur. The distal end of the rod may have flutes 60 to increase the surface area of the junction between the rod and the intramedullary canal of the femur. The distal end of the rod may also have a slot (not shown) along the longitudinal axis of the rod to better accommodate the internal anomalies occurring in the interior of the intramedullary canal. This structure allows the distal end of the rod to compress to a smaller diameter to more easily reach the desired depth of insertion.

The trochanter element 16 is mounted on the proximal end of the intramedullary rod. The trochanter has a through bore portion 17 in the distal end thereof through which the proximal end 13 of the intramedullary rod is inserted. As shown in FIG. 3, the through bore portion 17 and the proximal end 13 of the intramedullary rod have corresponding mating surfaces which lock the elements together preventing any rotational movement. The bore portion 17 has planar opposite sides 18 and 19 and curved surfaces 20 and 21 joining the ends of the planar sides. The proximal end of the intramedullary rod is sized to closely fit within the bore portion 17. The proximal end of the intramedullary rod also has opposite planar sides 22 and 23 joined by curved surfaces 24 and 25.

Because the intramedullary rod 11 and trochanter 16 do not move rotationally, it is very important that the orientation of the proximal end of the rod be established during insertion of the rod into the femur. Intramedullary rod 11 provides stability and the trochanter 16 acts as the load bearing element. As mentioned earlier, these components may be provided in different lengths and diameters. The proper insertion of the rod allows the immovable connection of the trochanter to the intramedullary rod in the approximate original position of the excised head of the femur.

In addition to or in place of the complementary surfaces in bore 17 and the proximal end 13 of the intramedullary rod, the bore portion 17 may be formed with a taper 26 which is smaller toward the proximal end of the trochanter and larger at the distal end. The proximal end of the intramedullary rod may be formed with a slightly larger diameter taper 27 having a smaller end toward the proximal end. As the two elements are telescoped together, the tapered walls engage each other further strengthening the connection between the elements.

The cooperating tapers 26 and 27 establish a precise limit to the distance the trochanter may be telescoped over the intramedullary rod. This limit, in turn, establishes the overall length of the two elements.

The proximate end of the intramedullary rod has a threaded bore 52 (shown in FIG. 6) for receiving the threaded end of compression screw 50.

The proximal end of trochanter 16 has a counter bore portion 30 which has a greater diameter than the diameter of the through bore portion 17 in the distal end. Counter bore portion 30 receives the conical distal end 31 of the neck element 40. The conical wall of the counter bore portion 30 tapers from a large diameter proximal end toward the distal end.

Initially, the counter bore portion 30 establishes a rotationally adjustable connection with the neck 40. This telescoped connection permits the neck to be adjusted relative to the trochanter to approximate the natural location of the original hip joint ball. The horizontal angle between the neck and the trochanter is the anteversion angle A, shown in FIG. 5.

The trochanter is shaped like the natural femur head and has an outer diameter that is larger than the intramedullary rod at the distal end. The distal end of the trochanter is inserted into the intramedullary canal. This junction of the trochanter and the shaft of the femur is the primary load carrying connection between the prosthesis and the patient's body. The trochanter flares to a larger diameter proximal end which has a planar surface 32 containing the counter bore portion 30.

The neck 40 has a partially cylindrical body 41 with a laterally extending arm 46 extending from the proximal surface of the body 41. This arm 46 carries the ball joint (not shown) for an artificial hip and can be specifically set at different anteversion angles to the trochanter and thus the axis of the femur.

Figure 7:
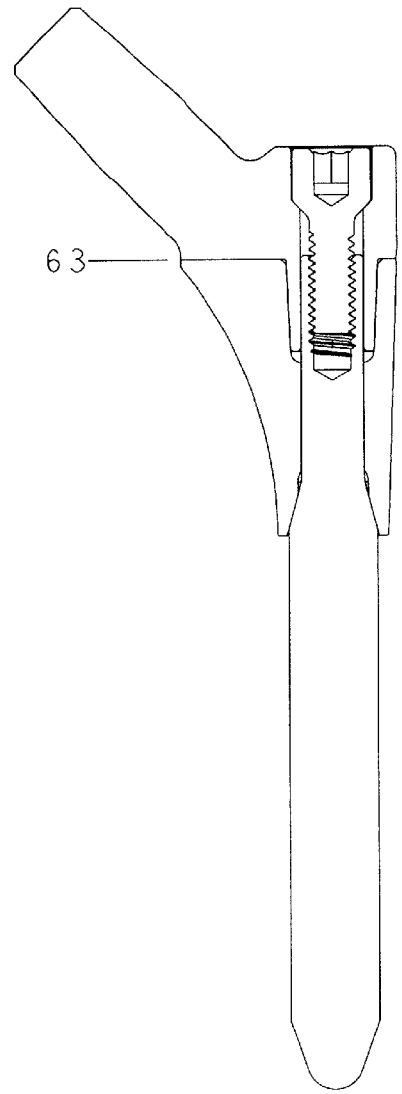
FIG. 7 shows a cross section of the finally assembled prosthesis without the visual gap.

The distal surface of the neck is formed as a flat surface 43 with a depending smaller conical distal end 31. After final assembly, the surfaces of the conical distal end 31 and the tapered through bore 30, as well as, the flat surface 43 and the surface 32 are in intimate contact throughout, as shown in FIG. 7.

Initially, the conical distal end 31 is telescoped into the tapered counter bore portion 30 of the trochanter. The conical surfaces of the distal end 31 and the through bore portion 30 are opposite and complementary. The depth of the through bore portion 30 is slightly greater than the height of the conical distal end 31 so that a friction fit is established when the elements are telescoped together. There is a space 62 in the through bore portion 30. Surface 43 of the neck and surface 32 of the body or trochanter are separated by a gap 61. This maintains the rotational axis relationship between the elements for final adjustments to fit a particular patient.

The neck has a bore 44 extending from the proximal end through the distal end 31. The proximal end 45 of the bore 44 is countersunk to receive the head of the bolt 50. The distal end of bore 44 receives the proximal end 13 of the intramedullary rod 11.

After the particular elements of the modular joint have been selected in reference to the patient's anatomy and the required surgical excision, the initial assembly is performed as described above.

The prosthesis 10 is then placed in a press or jig (not shown) which exerts substantial compression on the prosthesis without deforming the elements. This compression results in relative longitudinal movement between the neck 40 and the body or trochanter 16 that closes the gap 61 and creates an area seal throughout the complementary surfaces of the neck and the through bore. The area seal prevents pivoting or rotational movement between the neck 40 and the body 16. The juncture between the neck and body is a line 63.

The prosthesis is finally assembled by turning the threads of the compression screw 50 into the threads 52 of the intramedullary rod. As these cooperating screw threads tighten, a stop limit is formed between the intramedullary rod 11 and the neck 40. This stop limit may be set as a specific amount of ft-lbs of torque. Since the threads are not pulling element together but merely fixing them, the stress is more evenly distributed over the length of the shaft of the screw.

In the final disposition, the trochanter and the intramedullary rod are rotationally locked together over a major portion of their telescoped length because of their cooperating planar surfaces. The trochanter and the rod are longitudinally locked together by the compression screw through the neck and trochanter into the rod. The neck and the trochanter are rotationally and longitudinally locked together by the compression fit between their tapered surfaces. This fit is reinforced by the compression screw through the neck into the rod.

The various elements or components of the prosthesis may be made in different external sizes so that a range of elements is available to meet the size needs of various patients. However, the interconnecting portions of the different sized components are of the same size or, at least, made in a range of sizes so that the different external sized elements may be securely connected as described above.

What is claimed is:

1. A modular prosthesis to be used in joint replacement comprising:

an intramedullary rod having a distal end adapted for insertion into the intramedullary canal of a bone and a smaller proximal end, said proximal end having a smaller circumference than said distal end, said proximal end formed with opposite planar surfaces about said circumference, said proximal end having a screw threaded blind bore along a longitudinal axis of said intramedullary rod, a body having a narrow distal end and a larger proximal end, said larger proximal end having a flat surface, said body having a shaped through bore with a varying circumference from said distal end to said proximal end, a proximal portion of said shaped through bore having a tapered wall, another portion of said shaped through bore having opposite planar surfaces about said varying circumference, said planar surfaces of said bore and said planar surfaces of said proximal end of said intramedullary rod adapted to telescope together forming a rotationally secure connection, a neck having a flat surface at said distal end with a conical extension extending therefrom adapted to be inserted into said proximal portion of said tapered through bore of said body, said conical extension on said distal end of said neck and said tapered proximal end of said shaped through bore in said body adapted to telescope together to form an area seal throughout the contacting surfaces of said conical extension and said tapered through bore providing a rigid connection, said neck having a through bore, said proximal end of said through bore having a larger countersunk bore, said distal end of said through bore exiting said conical extension and adapted to telescope over the proximal end of said intramedullary rod, and a threaded compression screw adapted to be disposed in said countersunk bore and threadably engaged with said screw threads in said proximal end of said intramedullary rod forming a locked integral prosthesis.

2. A modular prosthesis as claimed in claim 1 wherein said proximal end of said intramedullary rod has opposite planar surfaces connected by curved surfaces, said shaped through bore of said body having opposite planar surfaces connected by curved surfaces, said proximal end of said intramedullary rod and said through bore of said body adapted to be telescoped together with said planar surfaces and said curved surfaces in intimate contact with each other.

3. A modular prosthesis as claimed in claim 2 wherein said distal end of said shaped through bore in said body has a tapered surface and said proximal end of said intramedullary rod has a tapered surface, said tapered surfaces forming a stop limit when said intramedullary rod and said body are telescoped together.

4. A modular prosthesis as claimed in claim 1 wherein said prosthesis is a hip joint and said body is a trochanter, said conical extension of said neck and said proximal end of said tapered through bore in said trochanter each have complementary tapered surfaces forming an area seal connection between said neck and said trochanter when substantial compression force is applied to said prosthesis.

5. A modular prosthesis as claimed in claim 1 wherein said prosthesis is a hip joint and said body is a trochanter, said conical extension of said neck and said proximal end of said tapered through bore in said trochanter each have complementary tapered surfaces forming an area seal connection between said neck and said trochanter, said proximal flat surface of said trochanter contacts said distal flat surface of said neck when substantial compression force is applied to said prosthesis.

6. A modular prosthesis of claim 3 wherein a plurality of different sized intramedullary rods, bodies, necks and compression screws are provided in a kit, said plurality of intramedullary rods, bodies, necks, and compression screws being adapted for interchangeable assembly to form a particular prosthesis with specific characteristics.

7. A method of assembly of the modular prosthesis of claim 5 comprising the steps of;

a) selecting a particular sized intramedullary rod, b) selecting a particular sized body, c) selecting a particular sized neck, d) telescoping said proximal end of said intramedullary rod into said shaped through bore of said body and engaging the planar surfaces on said proximal end of said intramedullary rod and said planar surfaces of said shaped through bore of said body forming a rotationally secure connection between said intramedullary rod and said body, e) determining the horizontal angle of said body resulting from the insertion of said intramedullary rod in a bone, f) telescoping said conical extension of said neck into the proximal tapered through bore of said body forming a friction fit between said body and said neck and establishing a visual gap between said body and said neck, g) adjusting the anteversion angle between said horizontal angle of said body about said intramedullary rod and said horizontal angle of said neck to said body to replicate a bone, h) applying substantial longitudinal pressure to said prosthesis to create a rigid area seal between said conical extension and said tapered through bore and eliminating said visual gap, and i) threading a compression screw into said threaded blind bore of said intramedullary rod and setting said screw at a particular torque.

* * * * *

UNITED STATES PATENT AND TRADEMARK OFFICE
CERTIFICATE OF CORRECTION

PATENT NO.     : 6,355,068 B1
DATED          : March 12, 2002
INVENTOR(S)    : Doubler et al.

It is certified that error appears in the above-identified patent and that said Letters Patent is hereby corrected as shown below:

<u>Column 8,</u>
Line 17, insert after "sis,"
-- wherein said conical extension and said tapered proximal portion of said through bore are telescoped together, said flat surface on said proximal end of said body spaced apart from said flat surface on said distal end of said neck forming a visual gap whereby said visual gap forms a sight gauge. --

Signed and Sealed this

Twenty-fifth Day of November, 2003

JAMES E. ROGAN
*Director of the United States Patent and Trademark Office*